(12) United States Patent
Guo (10) Patent No.: US 10,712,268 B2
(45) Date of Patent: Jul. 14, 2020

(54) TURN-ON NEAR INFRARED FLUORESCENT PROBES FOR IMAGING LYSOSOMAL ROS IN LIVE CELLS AT SUBCELLULAR RESOLUTION

(71) Applicant: UNIVERSITY OF MASSACHUSETTS, Boston, MA (US)

(72) Inventor: Maolin Guo, Dartmouth, MA (US)

(73) Assignee: University of Massachusetts, Boston, MA (US)

( * ) Notice: Subject to any disclaimer, the term of this patent is extended or adjusted under 35 U.S.C. 154(b) by 178 days.

(21) Appl. No.: 15/764,819

(22) PCT Filed: Oct. 4, 2016

(86) PCT No.: PCT/US2016/055336
§ 371 (c)(1),
(2) Date: Mar. 29, 2018

(87) PCT Pub. No.: WO2017/062364
PCT Pub. Date: Apr. 13, 2017

(65) Prior Publication Data
US 2019/0041331 A1 Feb. 7, 2019

Related U.S. Application Data

(60) Provisional application No. 62/239,344, filed on Oct. 9, 2015.

(51) Int. Cl.
*C07D 405/06* (2006.01)
*G01N 21/64* (2006.01)
*A61K 49/00* (2006.01)
*G01N 31/22* (2006.01)

(52) U.S. Cl.
CPC ..... *G01N 21/6428* (2013.01); *A61K 49/0019* (2013.01); *C07D 405/06* (2013.01); *G01N 31/228* (2013.01); *G01N 2021/6439* (2013.01)

(58) Field of Classification Search
None
See application file for complete search history.

(56) References Cited

U.S. PATENT DOCUMENTS

| 2010/0081159 A1 | 4/2010 | Lebedeva et al. | 435/29 |
| 2014/0105826 A1 | 4/2014 | Murthy et al. | 424/9.6 |
| 2015/0192564 A1 | 7/2015 | Lebedeva et al. | 435/29 |

OTHER PUBLICATIONS

Andina, D. et al. (2017) "Ratiometric Fluorescent Probes for the Detection of Reactive Oxygen Species," *Chemistry—A European Journal* 23(55), 13549-13573.
Barnham, K. J. et al. (2004) "Neurodegenerative diseases and oxidative stress," *Nature Reviews Drug Discovery* 3(3), 205-214.
Chan, J. et al. (2012) "Reaction-based small-molecule fluorescent probes for chemoselective bioimaging," *Nature Chemistry* 4, 973.
Chen, X. et al. (2011) "Fluorescent and luminescent probes for detection of reactive oxygen and nitrogen species," *Chemical Society Reviews* 40(9), 4783-4804.
Dickinson, B. C. et al. (2010) "Mitochondrial-targeted fluorescent probes for reactive oxygen species," *Current Opinion in Chemical Biology* 14(1), 50-56.
Kim, D. et al. (2015) "Visualization of Endogenous and Exogenous Hydrogen Peroxide Using a Lysosome-Targetable Fluorescent Probe," *Scientific Reports* 5.
Kundu, K. et al. (2009) "Hydrocyanines: A Class of Fluorescent Sensors That Can Image Reactive Oxygen Species in Cell Culture, Tissue, and In Vivo," *Angewandte Chemie International Edition* 48(2), 299-303.
Li, L. et al. (2014) "Sensitive and Selective Near-Infrared Fluorescent Off-On Probe and Its Application to Imaging Different Levels of β-Lactamase in Staphylococcus aureus," *Analytical Chemistry* 86(12), 6115-6120.
Wang, X. et al. (2013) "Imaging ROS signaling in cells and animals," *Journal of Molecular Medicine* 91(8), 917-927.
Wardman, P. (2007) "Fluorescent and luminescent probes for measurement of oxidative and nitrosative species in cells and tissues: Progress, pitfalls, and prospects," *Free Radical Biology and Medicine* 43(7), 995-1022.
Wei, Y. et al. (2010) "A novel profluorescent probe for detecting oxidative stress induced by metal and H2O2 in living cells," *Chemical Communications* 46(25), 4472-4474.
Winterbourn, C. C. (2008) "Reconciling the chemistry and biology of reactive oxygen species," *Nature Chemical Biology* 4(5), 278-286.
Woolley, J. F. et al. (2013) "Recent advances in reactive oxygen species measurement in biological systems," *Trends in Biochemical Sciences* 38(11), 556-565.
Wrobel, A. T. et al. (2014) "A fast and selective near-infrared fluorescent sensor for multicolor imaging of biological nitroxyl (HNO)," *Journal of the American Chemical Society* 136(12), 4697-4705.
Yuan, L. et al. (2012) "A Unique Approach to Development of Near-Infrared Fluorescent Sensors for in Vivo Imaging," *Journal of the American Chemical Society* 134(32), 13510-13523.
PCT International Search Report of International Application No. PCT/US2016/055336 dated Jan. 31, 2017.

*Primary Examiner* — Heidi Reese
(74) *Attorney, Agent, or Firm* — Medlen & Carroll, LLP

(57) ABSTRACT

This invention is in the field of fluorescence imaging and relates to a new near infrared (NIR) reactive oxygen species (ROS) sensor designed with controlled fluorescence on-off switching mechanism.

10 Claims, 9 Drawing Sheets

FIGURE 1

Prior Art

DCF-DA  DHE  DHR-123

FIGURE 2

(*E*)-2-(2-(6-hydroxy-2,3-dihydro-1*H*-xanthen-4-yl)vinyl)-3,3-dimethyl-1-propyl-3*H*-indol-1-ium iodide

TURN-ON NEAR INFRARED FLUORESCENT PROBES FOR IMAGING LYSOSOMAL ROS IN LIVE CELLS AT SUBCELLULAR RESOLUTION

CROSS-REFERENCE TO RELATED APPLICATIONS

The present application claims the benefit of U.S. Provisional Patent Application No. 62/239,344, filed on Oct. 9, 2015, which is incorporated herein by reference.

FIELD OF THE INVENTION

This invention is in the field of fluorescence imaging and relates to a new near infrared (NIR) reactive oxygen species (ROS) sensor designed with controlled fluorescence on-off switching mechanism.

BACKGROUND OF THE INVENTION

With the quick and significant growth of interest in function and control of free radicals in biology species, a tool to measure either the integrated production rates or the steady-state concentrations, and to visualize the spatial distribution has become a need. Compounds that can help visualize such free radicals would be extremely useful understanding the role free radicals may play in cellular processes, dysfunction, and disease.

SUMMARY OF THE INVENTION

This invention is in the field of fluorescence imaging and relates to a new near infrared (NIR) reactive oxygen species (ROS) sensor designed with controlled fluorescence on-off switching mechanism.

In one embodiment, the invention relates to a compound with the structure:

wherein A and Z are each independently selected from the group consisting of C, Si, N, P, O, S, and Se; n=0, 1, 2, 3, or 4; $R^1$ to $R^7$ are each independently selected from the group consisting of H, F, Cl, Br, I, alkyl, arylalkyl, alkoxy, aryloxy, alkylamino, an amino, an azido, a carboxy, cyano, hydroxyl, nitro, phosphate, solfo, sulfate, a nitrogen heterocycle, an oxygen heterocycle, or a sulfur heterocycle; $R^8$ to $R^{10}$ are each independently selected from the group consisting of H or D, in either S or R, or cis- or trans-conformation/configuration; and $R^{11}$ to $R^{17}$ are each independently selected from the group consisting of H, F, Cl, Br, I, alkyl, arylalkyl, alkoxy, aryloxy, alkylamino, an amine, an imine, an amino, an azido, a carboxy, cyano, hydroxyl, nitro, phosphate, solfo, sulfate, a nitrogen heterocycle, an oxygen heterocycle, and sulfur heterocycle.

In one embodiment, the invention relates to a method of monitoring reactive oxygen species, comprising: a) providing i) a fluid comprising at least one reactive oxygen species; ii) a fluorescent sensor compound comprising the formula of:

wherein A and Z are each independently selected from the group consisting of C, Si, N, P, O, S, and Se; n=0, 1, 2, 3, or 4; $R^1$ to $R^7$ are each independently selected from the group consisting of H, F, Cl, Br, I, alkyl, arylalkyl, alkoxy, aryloxy, alkylamino, an amino, an azido, a carboxy, cyano, hydroxyl, nitro, phosphate, solfo, sulfate, a nitrogen heterocycle, an oxygen heterocycle, or a sulfur heterocycle; $R^8$ to $R^{10}$ are each independently selected from the group consisting of H or D, in either S or R, or cis- or trans-conformation/configuration; and $R^{11}$ to $R^{17}$ are each independently selected from the group consisting of H, F, Cl, Br, I, alkyl, arylalkyl, alkoxy, aryloxy, alkylamino, an amine, an imine, an amino, an azido, a carboxy, cyano, hydroxyl, nitro, In one embodiment, the invention relates to a compound with the structure:

phosphate, solfo, sulfate, a nitrogen heterocycle, an oxygen heterocycle, and sulfur heterocycle, b) introducing said fluorescent sensor compound into said fluid; c) collecting fluorescent light data from said fluorescent sensor compound; and d) producing a superior spatial resolution photo image of said biological system using said fluorescent light data. In one embodiment, said fluorescent sensor compound comprises In one embodiment, said fluid comprises a biological fluid system comprising a plurality of basal reactive oxygen species.

In one embodiment, the invention relates to a method for profiling the status of biologically reactive oxygen species in living cells or subcellular organelles, or both, said method comprising the steps of: a) providing: i) at least one sample of said living cells comprising a plurality of cellular organelles; and ii) a selective reactive species indicator probe for detecting a plurality of biologically reactive species selected from the group consisting of specific reactive oxygen species and specific reactive nitrogen species; b) contacting said sample with said selective indicator probe, wherein said probe generates fluorescent signals; and c) measuring said fluorescent signals, thereby providing a profile status of said plurality of biologically reactive species. In one embodiment, said reactive indicator probe is:

wherein A and Z are each independently selected from the group consisting of C, Si, N, P, O, S, and Se; n=0, 1, 2, 3, or 4; $R^1$ to $R^7$ are each independently selected from the group consisting of H, F, Cl, Br, I, alkyl, arylalkyl, alkoxy, aryloxy, alkylamino, an amino, an azido, a carboxy, cyano, hydroxyl, nitro, phosphate, solfo, sulfate, a nitrogen heterocycle, an oxygen heterocycle, or a sulfur heterocycle; $R^8$ to $R^{10}$ are each independently selected from the group consisting of H or D, in either S or R, or cis- or trans-conformation/configuration; and $R^{11}$ to $R^{17}$ are each independently selected from the group consisting of H, F, Cl, Br, I, alkyl, arylalkyl, alkoxy, aryloxy, alkylamino, an amine, an imine, an amino, an azido, a carboxy, cyano, hydroxyl, nitro, phosphate, solfo, sulfate, a nitrogen heterocycle, an oxygen heterocycle, and sulfur heterocycle. In one embodiment, said reactive indicator probe is:

In one embodiment, said living cells are isolated from a biological material selected from a tissue, an organ or an organism. In one embodiment, said subcellular organelles are selected from the group consisting of mitochondria, peroxisomes, cytosol, vesicles, lysosomes, plasma membranes, chloroplasts, nuclei, nucleoli, inner mitochondrial matrices, inner mitochondrial membranes, intermembrane spaces, outer mitochondrial membranes, secretory vesicles, endoplasmic reticuli, golgi bodies, phagosomes, endosomes, exosomes, plasma membranes, microtubules, microfilaments, intermediate filaments, filopodia, ruffles, lamellipodia, sarcomeres, focal contacts, podosomes, ribosomes, microsomes, lipid rafts, nuclear membranes, chloroplasts or cell walls, and combinations thereof In one embodiment, said probe reacts with reactive oxygen species (ROS) selected from the group consisting of superoxide ($O_2\bullet-$), hydrogen peroxide ($H_2O_2$), peroxynitrite (ONOO—), hydroxyl radical (HO$\bullet$), tert-butoxide (TBO), tert-butyl hydroperoxide (TBHP), and combinations thereof. In one embodiment, said probe localizes within at least one of said subcellular organelle. In one embodiment, said subcellular organelle is at least one lysosome. In one embodiment, said profile status comprises a profile of basal biological reactive species levels. In one embodiment, said profile status comprises a profile of subcellular organelle biological reactive species levels.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" as used herein, in the context of any of any assay measurements refers to +/−5% of a given measurement.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that all trace impurities have been removed.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatiblity is evaluated according to the application for which it was designed: for example; a bandage is regarded a biocompable with the skin, whereas an implanted medical device is regarded as biocompatible with the internal tissues of the body. Preferably, biocompatible materials include, but are not limited to, biodegradable and biostable materials.

As used herein, the term "reactive oxygen species (ROS)" is used throughout the specification to describe chemically reactive molecules containing oxygen. Examples include peroxides. superoxide, hydroxyl radical, and singlet oxygen. ROS are formed as a natural byproduct of the normal metabolism of oxygen and have important roles in cell signaling and homeostasis. However, during times of environmental stress (e.g., UV or heat exposure), ROS levels can increase dramatically. This may result in significant damage to cell structures. Cumulatively, this is known as oxidative stress. ROS are also generated by exogenous sources such as ionizing radiation.

As used herein, the term "superior spatial resolution" refers to that images with a better spatial resolution compared with other bioimages of ROS typically reported. For example, by using the RTMI probe, confocal images of cellular ROS can be obtained at subcellular resolution, i.e., ROS at specific organelles in cells. While images with other ROS probes often achieve resolutions at tissue or cellular level only.

DESCRIPTION OF THE FIGURES

The file of this patent contains at least one drawing executed in color. Copies of this patent with color drawings will be provided by the Patent and Trademark Office upon request and payment of the necessary fee.

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 8A&B shows representative microscopic imaging of detection of ROS in BAEC by RTMI.

FIG. 9A-H shows representative confocal images of intracellular studies of ROS sensor RTMI incubated in Bovine Aortic Endothelial Cells (BAEC) preloaded with TBHP (100 µM) 30 min, and then replace with fresh media containing RTMI (10 µM) for 30 min, and then co-labeled with Mito Tracker Green and Lyso Tracker Blue. FIG. 9A shows DIC image; FIG. 9B shows RTMI only; FIG. 9C shows Lyso Tracker Blue; FIG. 9D shows Mito Tracker Green; FIG. 9E shows an overlay of FIG. 9C and FIG. 9D; FIG. 9F shows an overlay of FIG. 9B and FIG. 9C; FIG. 9G sows an overlay of FIG. 9B and FIG. 9D; FIG. 9H shows an overlay of FIG. 9B and FIG. 9C and FIG. 9D.

DESCRIPTION OF THE INVENTION

1. Background

Reactive Oxygen Species (ROS) are oxygen metabolites that are highly active in terms of oxidative modifications of cellular macromolecules including, but not limited to, DNA, proteins and/or lipids. Typical reactive species include, but are not limited to, hydrogen peroxide ($H_2O_2$), lipid peroxides, hydroxyl, superoxide, peroxyl and organic alkoxyl radicals, carbonate radical-anion and/or peroxynitrite ($ONOO^-$). Although it is not necessary to understand the mechanism of an invention, it is believed that of all cellular ROS sources, electron leakage from the mitochondrial electron transport chain (ETC) to molecular oxygen generates a steady flux of superoxide and other ROS thus constitutes the major site of cellular ROS production. It is also believed that other enzymes, including NADPH oxidases, lipoxygenase and cyclooxygenase, cytochrome p450s, and xanthine oxidase, also participate in ROS generation [1].

ROS have been long known related to health and diseases. ROS are produced during physiological and pathological processes and react with cellular components such as amino acids, proteins, lipids and nucleic acids [2]. Normally, these reactions are advantageous to the system because they involve redox signaling, cell migration, proliferation and neurogenesis. However, during times of stress, ROS can participate in damaging reactions leading to exhaustive cellular damage. ROS may play roles in normal physiological processes, such as through redox regulation of protein phosphorylation, ion channels, and transcription factors. ROS are also involved in biosynthetic processes, including but not limited to thyroid hormone production and cross-linking of extracellular matrix. ROS may also act as cellular messengers, redox regulators, and, when in excess, oxidative stressors those are widely implicated in pathologies of cancer and cardiovascular and neurodegenerative diseases. ROS-related disease can be either due to a lack of ROS (e.g., chronic granulomatous disease, certain autoimmune disorders) or a surplus of ROS (e.g., cardiovascular and neurodegenerative diseases) [3].

Figure 1:
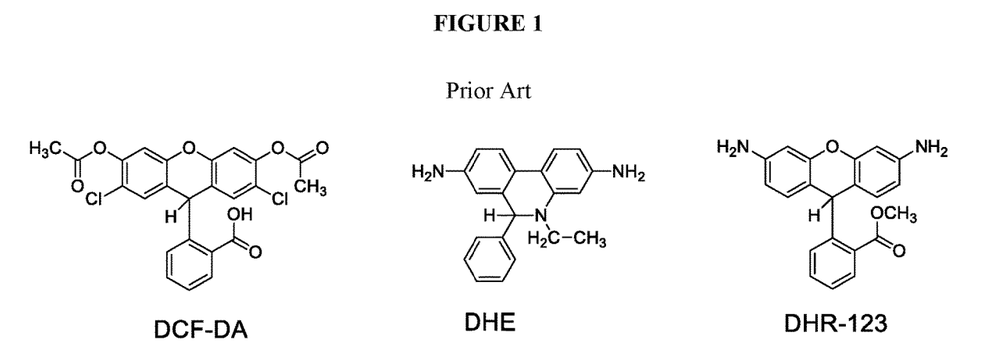
FIG. 1 shows a few recently developed ROS sensors.

There are significant interests in monitoring the in vitro and in vivo level of ROS. With the rapid and significant growth of interests in ROS in biology and medicine, a tool to measure either the integrated production or the steady-state level of ROS, and to visualize the spatial distribution has become an urgent need. Since fluorescence imaging has become a useful technique for monitoring biomolecules in living systems and fluorescent sensors have a lot potential for bioimaging, highly sensitive, rapidly responsive and reversible "turn-on" or ratiometric fluorescent sensors that are capable of ROS imaging with tempo and spatial resolution would be highly valued to the biomedical field. A few fluorescent sensors that can detect ROS in living systems have been available (FIG. 1). These sensors provide useful information on cellular ROS, however, they suffer from certain problematic issues.

Currently available fluorescent sensors have limited abilities to detect native cellular ROS and suffered from poor sensitivity, poor reactivity towards common cellular ROS, poor photostability (photo bleaching), short wavelength excitation/emission and other issues [4]. For example, DCF-DA and DHR-123 have very poor reactivity toward the common cellular ROS superoxide radicals and hydrogen peroxide. They can be activated by the Fenton Chemistry product hydroxyl radical, peroxynitrite and its decomposed products CO3● or NO2●, or some other enzyme catalyzed reactions. DHE has poor sensitivity and poor photo-stability.

None of the current ROS-detection systems can image basal level native ROS in live cells or at subcellular resolution due to their poor sensitivity and poor spatial resolution. There is a strong need for highly sensitive sensing systems for live-cell ROS imaging. Moreover, there are few ROS sensors with absorption and emission in the near-infrared (NIR) region (650-900 nm). NIR sensors are desired due to their decreased photo damage to biological samples, deeper tissue penetration, and decreased interference from background auto fluorescence by biomolecules in the living systems.

The detection of reactive oxygen species has been a goal in biochemistry and microbiology for some time. Several references have described such tools for detection. One reference, Wang, et al. (2013). Imaging ROS signaling in cells and animals. *Journal of Molecular Medicine,* 91(8), 917-927 [1] discloses the state of the art in detection of reactive oxygen species. The reference states that synthetic fluorescent probes are useful in detecting reactive oxygen species, but many of the probes have limitations related to selectivity, localization and wavelength. The reference calls for the development of small-molecule fluorescent ROS probes with improved selectivity, reversible kinetics and compartment-targeting property. The reference also describes the usefulness of the use of multiple probes at once for improved quantitative ability, and spatiotemporal resolution. The reference does not disclose the RTMI probe described in the invention disclosure.

Another reference, United States Patent Application Publication Number US 2010-0081159 A1 [5], discloses combinations of indicator probes, which in concert allow comprehensive profiling of reactive oxygen species (ROS) and reactive nitrogen species (RNS) and reactive halogen species (RHS) (and combinations of these species) in living cells and/or subcellular organelles. The reference describes incorporation of an indicator probe for global detection or measurement of oxidative and/or nitrative stress and/or halogenating stress, and two or more other indicator probes capable of more restrictive detection of specific ROS or RNS species, without substantial cross-reaction with other ROS or RNS. The reference later specifies lysosomes as organelles. The reference does not disclose the RTMI probe described in the invention disclosure.

Another reference, Kim, D. et al. (2015) Visualization of Endogenous and Exogenous Hydrogen Peroxide Using a Lysosome-Targetable Fluorescent Probe, Sci. Rep. 5 [6], discloses the use of a lysosome targetable fluorescent probe to visualize hydrogen peroxide. The fluorescent probe is a naphthalimide fluorophore with a morpholine moiety to direct the probe to the lysosome. This probe is significantly structurally different from RTMI. The reference does not disclose the RTMI probe described in the invention disclosure.

2. Near Infrared Reactive Oxygen Species (NIR ROS) Sensor Compounds (RTMI)

In one embodiment, the present invention contemplates a Near Infrared Reactive Oxygen Species (NIR ROS) Sensor compound (RTMI) with excellent reactivity to the biologically relevant common ROS (reactive oxygen species) that are capable of detecting basal ROS levels in live cells with subcellular resolution. The RTMI sensor compound does not absorb nor has fluorescence in the visible to near IR region. However, upon reacting with ROS in physiological buffer, strong fluorescence was observed at the near IR region with a peak centered at 705 nm. The RTMI sensor compound has broad reactivity towards ROS, including hydroxyl radical (HO●), superoxide radical, TBO, TBHP, $H_2O_2$ and peroxynitrite. However, it does not respond to $Fe^{2+}$, nitric oxide radical, nitrite, GSH or GSSG.

In one embodiment, the invention relates to NIR ROS sensor detection molecules with the structure:

wherein A and Z are each independently selected from the group consisting of C, Si, N, P, O, S, and Se; n=0, 1, 2, 3, or 4; $R^1$ to $R^7$ are each independently selected from the group consisting of H, F, Cl, Br, I, alkyl, arylalkyl, alkoxy, aryloxy, alkylamino, an amino, an azido, a carboxy, cyano, hydroxyl, nitro, phosphate, solfo, sulfate, a nitrogen heterocycle, an oxygen heterocycle, or a sulfur heterocycle; $R^8$ to $R^{10}$ are each independently selected from the group consisting of H or D, in either S or R, or cis- or trans-conformation/configuration; and $R^{11}$ to $R^{17}$ are each independently selected from the group consisting of H, F, Cl, Br, I, alkyl, arylalkyl, alkoxy, aryloxy, alkylamino, an amine, an imine, an amino, an azido, a carboxy, cyano, hydroxyl, nitro, phosphate, solfo, sulfate, a nitrogen heterocycle, an oxygen heterocycle, and sulfur heterocycle.

In one embodiment, the invention relates to the synthesis of a NIR ROS Sensor detection chemical by reacting IR780 with resorcinol to create the RTMI sensor compound, having the following structure:

Unlike other fluorescent sensors, the RTMI sensor is described as a superior approach because: It can detect lysosomal ROS with its superior spatial resolution while none other ROS sensor can do. It has excellent reactivity to a broad type of common ROS including, but not limited to, hydroxyl radical (HO●), superoxide radical, TBO., TBHP, $H_2O_2$, and/or peroxynitrite; while none other ROS sensor can detect such a broad type of ROS. It is uncharged and can diffuse through cell membrane easily and upon activated by ROS it become charged and stay in cells thus has excellent retention in cells. Moreover, it has very good photo stability and it absorbs and emits in the NIR region (>700 nm), a feature desired not interfering with cellular pigments and ideal for in vivo imaging. In one embodiment, said ROS sensor (RTMI) localizes to at least one lysosome.

Figure 2:
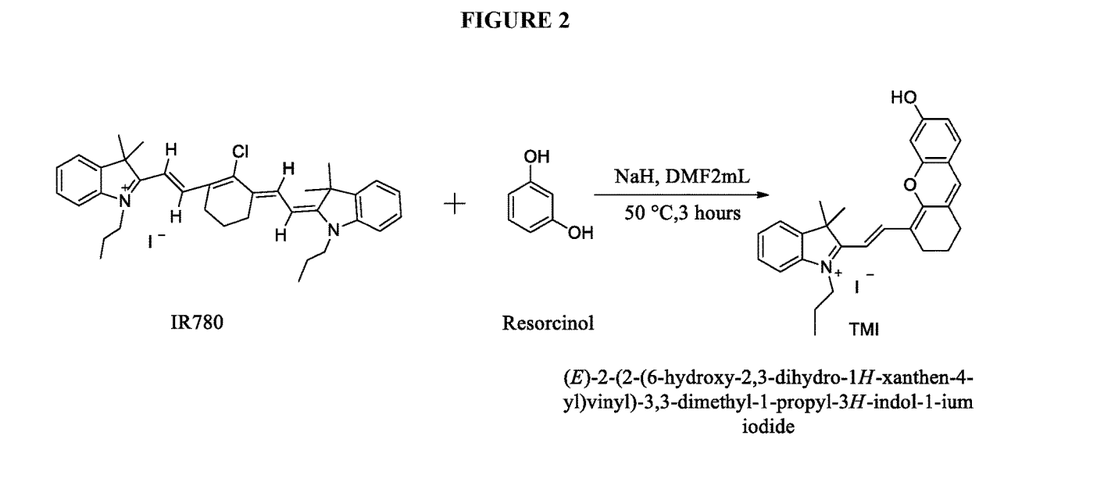
FIG. 2 shows a synthesis of TMI from IR780 and Resorcinol.
Figure 3:
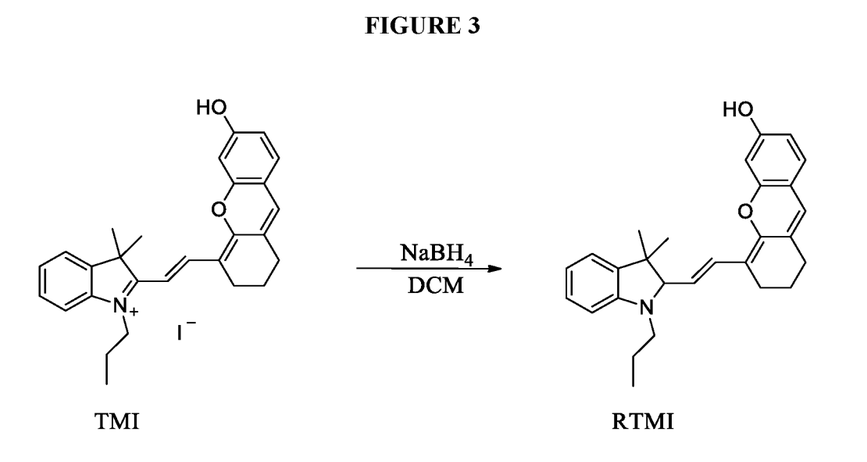
FIG. 3 shows the step of synthesizing TMI into ROS sensor RTMI.
Figure 4:
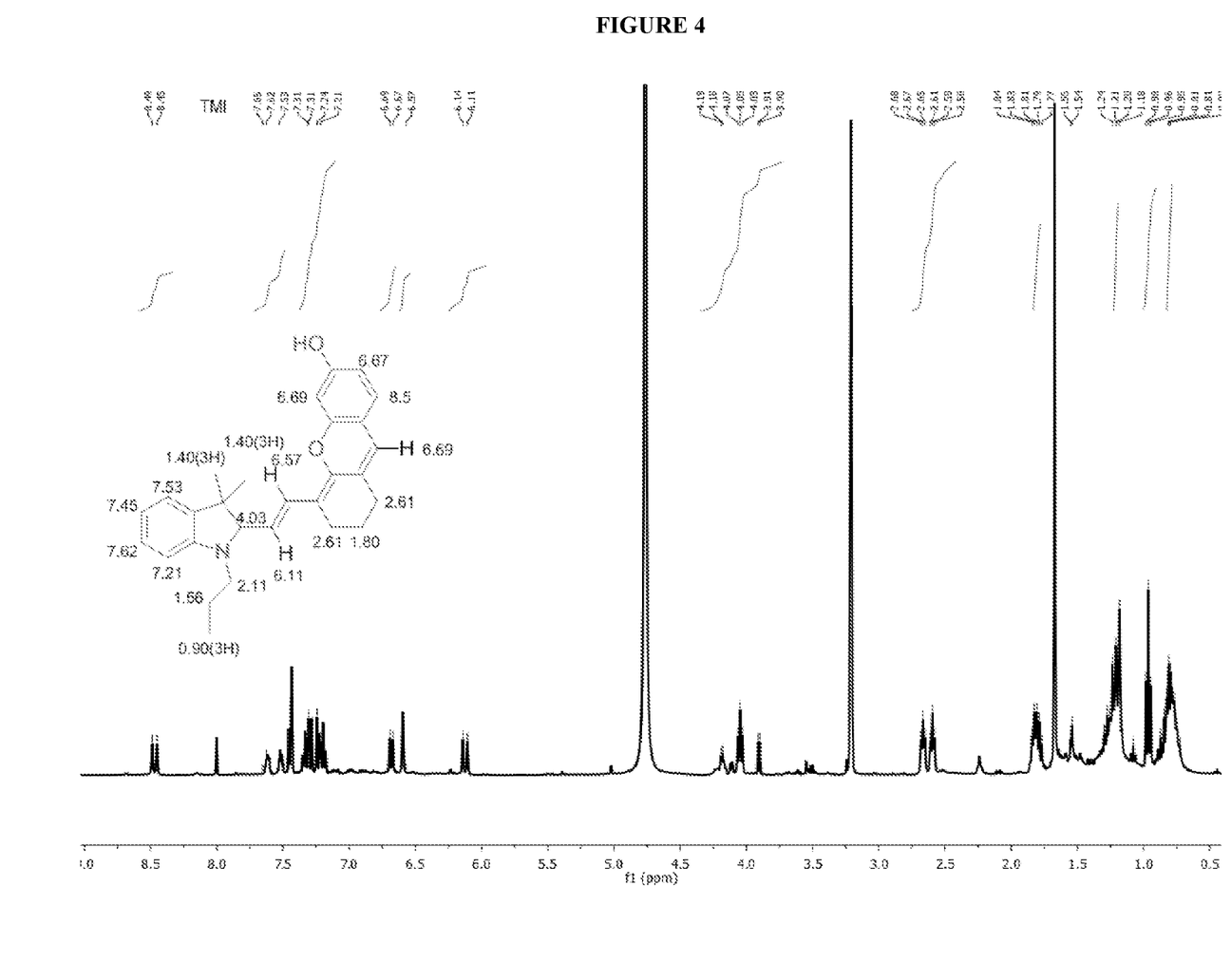
FIG. 4 shows the $^1$HNMR spectrum of RTMI in MeOD.
Figure 5:
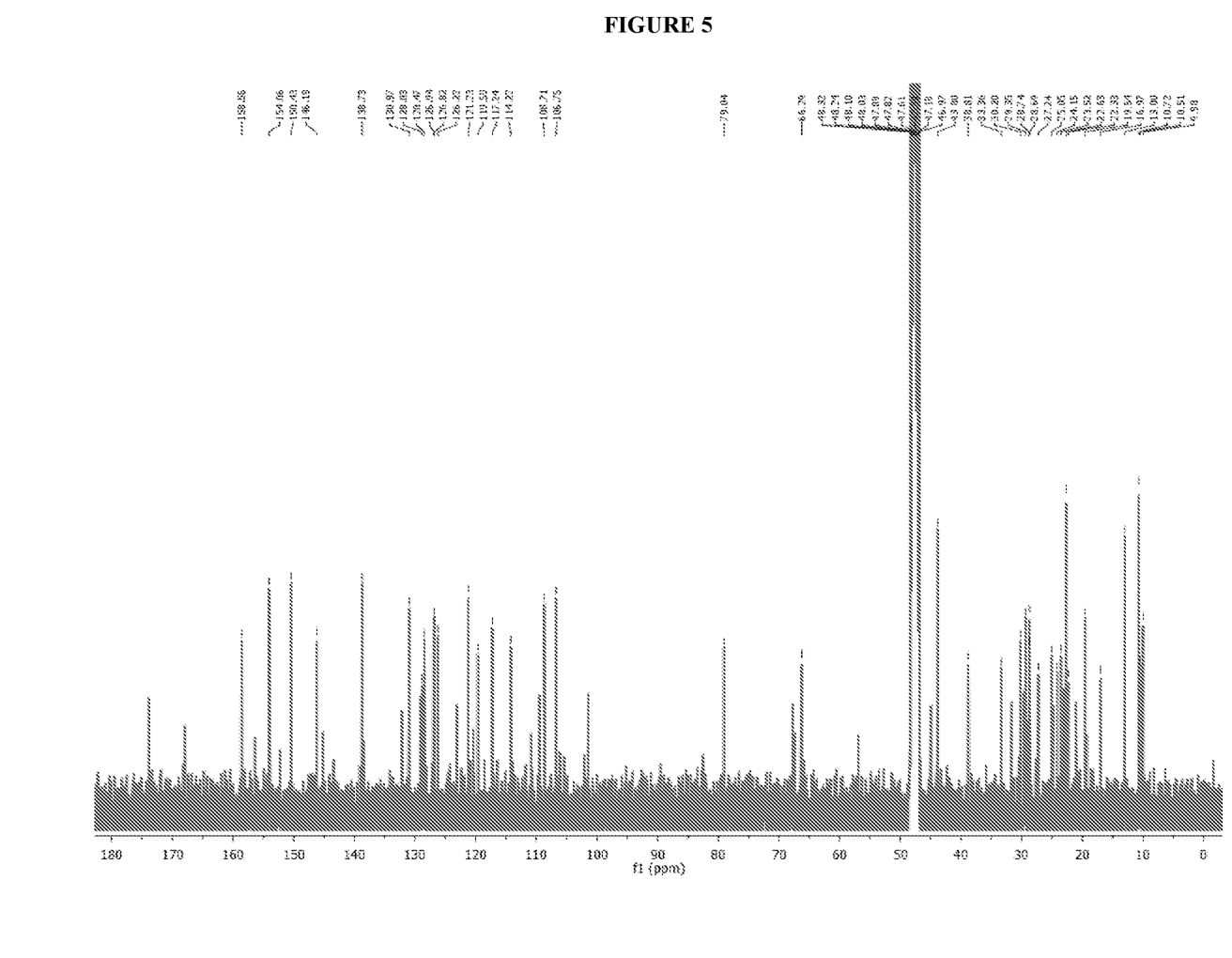
FIG. 5 shows the $^{13}$CNMR spectrum of RTMI in MeOD.

Described herein is one embodiment of the invention, an NIR ROS sensor (RTMI) with excellent reactivity to the biologically relevant common ROS that are capable of detecting lysosome ROS in live cells with subcellular resolution. In one embodiment, the ROS sensor (RTMI) is synthesized by a 2-step procedure from commercially available chemicals as summarized in FIG. 2 and FIG. 3, see Example 1.

The sensor RTMI does not absorb nor has fluorescence in the visible to near IR region. However, upon reacting with ROS in physiological buffer, strong fluorescence was observed at the near IR region with a peak centered at 705 nm. The RTMI probe has broad reactivity towards ROS, including but not limited to, hydroxyl radical (HO●), superoxide radical, TBO, TBHP, $H_2O_2$ and/or peroxynitrite. See FIG. 7. However, it does not respond to Fe2+, nitric oxide radical, nitrite, GSH or GSSG beyond baseline fluorescence.

Figure 8:
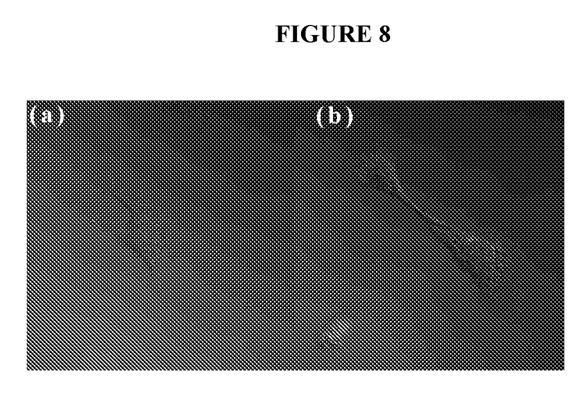
FIG. 8A shows BAEC incubated with RTMI (10 µM)
FIG. 8B shows BAEC incubated RTMI (10 µM) and $H_2O_2$ (100 µM).
Figure 9:
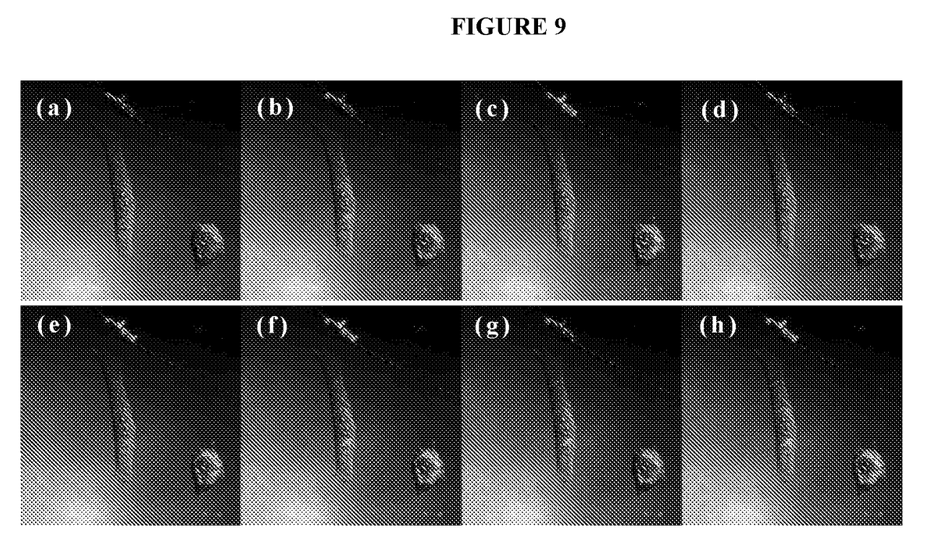

In one embodiment, the RTMI may be used to analyze ROS species within living systems. The RTMI sensor solution was applied to live cells and analyzed under a fluorescence microscope. Each of the various ROS (HO●, $H_2O_2$, $KO_2$, TBO, TBHP, peroxynitrite) or ROS inducer (ox-LDL) that were present combined with the RTMI sensor were incubated with BAEC cells. Compared to the control, the cells treated with ROS or ROS inducers showed strongly fluorescence emission signals in the near IR region detected by the fluorescent microscope (FIG. 8), demonstrating the ability of the RTMI sensor in detecting a broad types of ROS in live cells.

Co-localization experiments revealed the subcellular location of ROS detected by the RTMI sensor was in lysosomes, demonstrating the subcellular resolution imaging ability of the sensor, see FIG. 9A-H.

In summary, embodiments of the present invention comprise a new ROS sensor; RTMI. RTMI demonstrated "turn-on" responses with a broad type of common ROS including, but not limited to, hydroxyl radical (HO●), superoxide radical, TBO●, TBHP, $H_2O_2$ and/or peroxynitrite. The ability of RTMI to detect ROS has been demonstrated in live cells and ROS generation induced by Fe2+ and OX-LDL. The near infrared excitation and emission wavelength makes it an excellent NIR sensor for imaging ROS in living systems.

EXAMPLES

The following examples are provided in order to demonstrate and further illustrate certain preferred embodiments and aspects of the present invention and are not to be construed as limiting the scope thereof.

Example 1

Synthesis of ROS Sensor RTMI

Briefly, 15 mg (0.625 mmol) NaH (sodium hydride, 60% MW 24 g/mol) was placed in a flask under 0° C. Oxygen was removed and then replaced with argon and the device was sealed. 200 mg (1.816 mmol) resorcinol ($C_6H_6O_2$ >99%, MW 110.11) was dissolved in 2 ml DMF (N, N-Dimethylformamide, $C_3H_7NO$) and then introduced to the flask via a syringe. 250 mg (0.375 mmol) IR780 (IR-780 iodide, MW 667.11) was dissolved in 3 ml DMF and then introduced to the flask via syringe. The device was placed on a hot plate and the temperature was controlled at 50° C. After 3 hours, the system was cooled down to room temperature. The solution was poured to an ice-water mixture for precipitate. The crude product was filtered out for further purification via gel chromatography giving compound TMI as a blue solid (25 mg, yield 17%). Next, TMI (82 mg, 0.2 mmol) was dissolved in 5 mL dichloromethane, placed in a 4-drum vial covered with aluminum foil. $NaBH_4$ (3 mg, 0.08 mmol in 0.5 mL methanol) was added drop-wise to the blue TMI solution, stirred for 10 min, generating a colorless solution. Distilled water was added to react with the excess NaBH4. The reaction mixture was then stirred for additional 10 min. The organic layer was then extracted with additional dichloromethane (5 mL×2), dried over anhydrous sodium sulfate and the solvent was removed under reduced pressure to produce RTMI as an offyellow solid. TMI and RTMI were characterized by UV-vis, fluorescence, $^1$H NMR, $^{13}$C NMR and MS.

TMI $^1$H NMR (400 MHz, MeOD, FIGS. 3.1 and 3.2) δ 7.63 (d, J=50.2 Hz, 1H), 6.97 (dd, J=21.8, 9.5 Hz, 1H), 6.95-6.84 (m, 2H), 6.73 (d, J=19.0 Hz, 1H), 6.64 (d, J=7.5 Hz, 1H), 6.09 (s, 1H), 5.57-5.40 (m, 1H), 5.33 (d, 1H), 3.05-2.84 (m, 2H), 2.44-2.26 (m, 4H), 1.65 (m, 2H), 1.62 (s, 6H), 1.4 (m, 2H), 0.90 (s, 3H). $^{13}$C NMR (101 MHz, MeOD, (FIGS. 3.3)) δ 173.22 (s), 162.69 (s), 162.13 (s), 156.85 (s), 141.90 (s), 140.71 (s), 137.55 (s), 129.88 (s), 128.41 (s), 124.62 (s), 123.16 (s), 122.03 (s), 119.07 (s), 114.38 (s), 111.30-111.10 (m), 101.51 (s), 99.48 (s), 67.86 (s), 66.10 (s), 45.30 (s), 38.81 (s), 28.30 (s), 27.45 (s), 22.19 (s), 20.15 (s), 12.85 (s), 10.19 (s). LC/MS (positive mode), m/z, 412.6 for [M]$^+$ RTMI $^1$H NMR (400 MHz, MeOD, FIGS. 3.5-3.7) δ 8.47 (d, J=14.3 Hz, 1H), 8.13-7.86 (m, 1H), 7.62 (d, J=10.9 Hz, 1H), 7.53 (m, 1H), 7.50-7.39 (m, 1H), 7.21 (dd, J=31.9, 7.1 Hz, 1H), 6.67 (d, J=8.7 Hz, 1H), 6.57 (d, J=40.3 Hz, 1H), 6.12 (d, J=14.3 Hz, 1H), 4.05 (t, J=7.3 Hz, 1H), 2.63 (dt, J=28.7, 5.9 Hz, 4H), 1.91-1.75 (m, 3H), 1.70-1.61 (m, 3H), 1.55 (d, J=4.2 Hz, 1H), 0.84-0.75 (m, 3H). $^{13}$C NMR (101 MHz, MeOD) δ 158.56 (s), 154.06 (s), 150.43 (s), 146.19 (s), 138.73 (s), 130.97 (s), 128.65 (d, J=36.1 Hz), 127.11 (dd, J=119.1, 107.5 Hz), 121.23 (s), 119.38-118.61 (m), 117.24 (s), 114.22 (s), 108.71 (s), 106.66-105.72 (m), 78.81-77.11 (m), 66.29 (s), 43.80 (s), 38.81 (s), 33.36 (s), 30.20 (s), 28.72 (d, J=4.8 Hz), 25.05 (s), 22.88-19.48 (m), 16.97 (s), 13.00 (s), 10.92-9.46 (m), 9.46-7.00 (m). LC/MS (positive mode), m/z: 414.6 for [M+H]$^+$ Example 2

Materials for Synthesis and General Experiments

All the reagents and solvents were of the highest commercial quality and were used without further purification. All the solvents were of analytic grade. The solutions of reactive species were freshly prepared.

N,N-Dimethylformamide(DMF) anyhydrous (99.8% Sigma-Aldrich), 1,2-dichloro ethane anyhydrous (99.8% Sigma-Aldrich), and double-distilled water were used as solvents.

IR-780 iodide (dye content>98%) was purchased from Sigma-Aldrich. Resorcinol (>99%), sodium hydride (60%), sodium borohydride(NaBH4, >95%) were purchased from TCI America. Superoxide was purchased from Sigma Aldrichadded as solid $KO_2$.

Fresh solutions of L-ascorbic acid (50 mM), hydrogen peroxide (100 mM), tert-butyl hydrogen peroxide (TBHP, 100 mM), 3-morpholinosydnonimine (SIN-1, 5 mM), glutathione reduced form (GSH, 10 mM) and glutathione oxidized form (GSSG 10 mM) were prepared with distilled water.

3-(aminopropyl)-1- hydroxy-3-isopropyl-2-oxo-1-triazene (NOC-5, 1 mM) was made as a 10 mM sodium hydroxide solution and then added to the RTMI solution, to generate a 100 μM final concentration.

The hydroxyl and butoxyl radicals were generated in situ by reacting hydrogen peroxide or TBHP with $Fe^{2+}$. Fresh 10 mM $Fe^{2+}$ was made in 0.1 M HCl solution using ferrous ammonium sulfate [$Fe(NH_4)_2(SO_4)_2.6H_2O$]. A 10 μM RTMI solution, in PBS, containing 10 μM $Fe^{2+}$ was made and either hydrogen peroxide or TBHP was added to this solution to generate a 100 μM concentration.

Materials for Cell Experiments

The sensor RTMI was dissolved in DMF at a concentration of 10 mM. 1 μL of the DMF solution was added to cell medium without fetal bovine serum. Cell culture medium was removed from the cells in the culture dish and replaced with the fresh medium containing the sensor.

Oxidized low density lipoprotein (Ox-LDL, a stimulation factor for ROS production in cells) was dissolved in water solution and the final concentration in cell media was 20 μg/mL.

Commercial $H_2O_2$ (30% wt, density of 1.1 g/ml, MW 34.02 g/mol) was diluted with deionized water to make a fresh solution of 100 mM. 1 μL of the fresh solution was added to cell media to generate a final concentration of 100 μM.

SIN1(a peroxyitrite donor) was dissolved in deionized water to the concentration of 10 mM; 10 μL of this solution added to cell media to generate a final concentration of 100 μM.

$Fe^{2+}$ was freshly made from ferrous ammonium sulfate (MW 392.15 g/mol) dissolved in 0.1 M HCl (DI water solution) to generate a fresh solution of 100 mM. 1 μL of the fresh solution was added to cell media for incubation.

Commercial TBHP (70% wt, density of 0.935 g/ml, MW 90.12 g/mol) was used to make a fresh solution of 100 mM using deionized water. 1 μL of the fresh solution was added to generate a final concentration of 100 μM.

Primary cultured Bovine Aortic endothelial cells from bovine aorta were passaged in Dulbecco's modified Eagle's medium (DMEM) containing 10% fetal bovine serum and antibiotics. The cells were routinely subcultured using 0.05% trypsin-EDTA solution. The cells were seeded on 2-chamber slides for 48 hours at 5×10$^4$ cell/chamber and grown until each chamber was 20-30% confluent.

The BAEC cells were incubated for 30 min at 37° C. in DMEM containing sensor solution (serum free, DMF), and post incubation with DMEM was carried out for 1 hour in a humidified atmosphere with 5% CO2.

Confocal fluorescence imaging studies were performed with a Zeiss LSM 710 laser scanning microscope.

Instrumentation $^1$H and $^{13}$C NMR spectra were recorded on a Bruker AVANCE 400 MHz spectrometer. Chemical shifts are reported in delta (δ) unit per million (ppm) downfield tetramethylsilane. Splitting patterns are abbreviated as follows: s, singlet; d, doublet; t, triplet; q, quartet; m, multiplet; br, broad.

ESI-MS analyses were performed on a PerkinElmer API 150EX mass spectrometer. UV/Vis spectra were recorded on a Perkin-Elmer Lambda 25 spectrometers at 298 K.

Fluorescence spectra were recorded on a Perkin-Elmer LS55 luminescence spectrometer at 293 K. The excitation wavelengths and filters used were indicated in the figures.

The pH measurements were carried out on a Corning pH meter equipped with a Sigma-Adrich micro combination electrode calibrated with standard buffer solution.

Example 3

Fluorescent Responses of RTMI to Various ROS

Fluorescent responses of RTMI (100 μM) to various ROS were monitored in PBS, containing 1% methanol. Various reactive oxygen species were added to the 100 μM RTMI solutions, at a 5:1 molar ratio to RTMI, and the fluorescence intensity was recorded after 5 min of incubation at 25° C. Superoxide ($O_2^-$) was added as solid $KO_2$. Stock solution solutions of hydrogen peroxide, tert-butyl hydrogen peroxide (TBHP), hypochlorite, 3-morpholinosydnonimine (SIN-1), glutathione (GSH) and 1,4-hydroquinone were made and then added to the RTMI solution, to generate a 500 μM final concentration. 3-(aminopropyl)-1-hydroxy-3-isopropyl-2-oxo-1-triazene (NOC-5, 1 mM) was made as a 10 mM sodium hydroxide solution and then added to the RTMI solution, to generate a 500 μM final concentration. The hydroxyl and butoxyl radicals were generated in situ by reacting hydrogen peroxide or TBHP with $Fe^{2+}$. A 100 μM RTMI solution, in PBS, containing 500 μM $Fe^{2+}$ was made and either hydrogen peroxide or TBHP was added to this solution to generate a 500 μM concentration.

Figure 6:
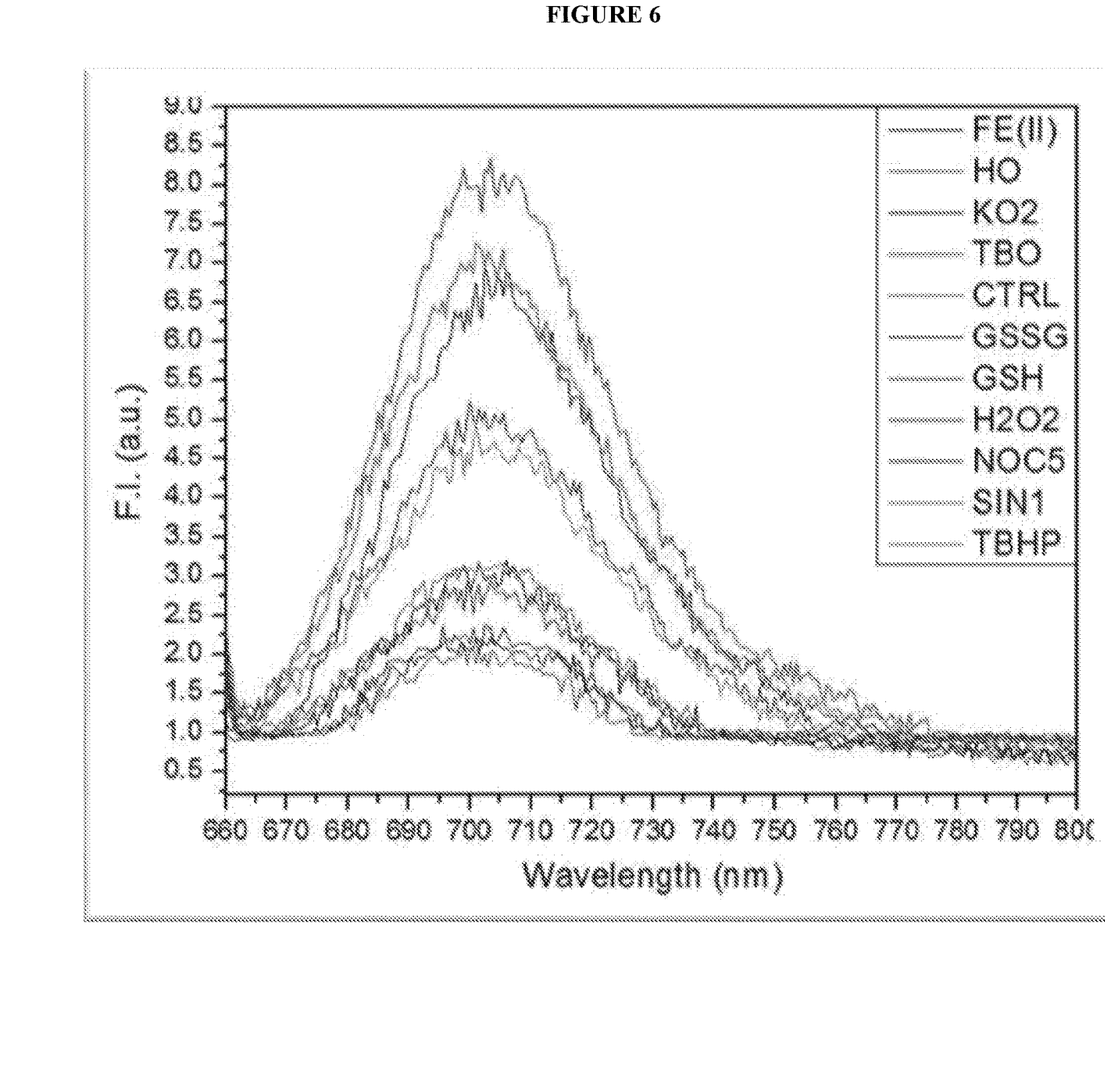
FIG. 6 shows fluorescent emission spectra of RTMI and its response to various ROS and RNS like $H_2O_2$, $NO_2^-$, $O_2^-$, OH, TBHP, GSH, TBO, GSSG and NOC-5.
Figure 7:
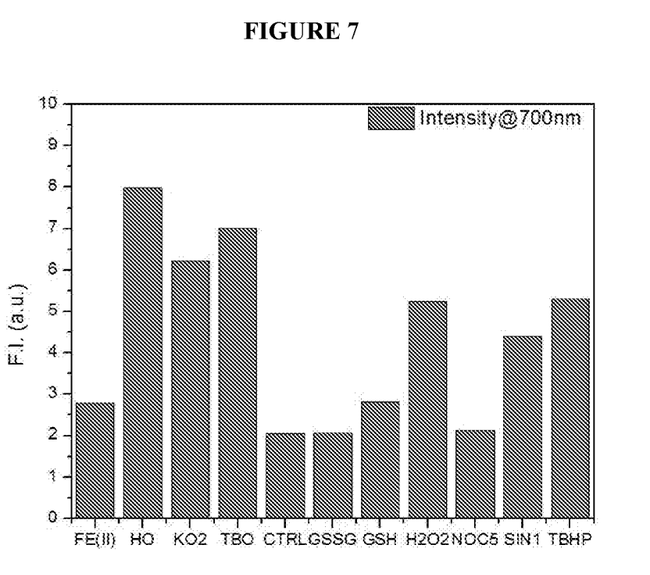
FIG. 7 shows fluorescent emission intensity of RTMI at $\lambda=700$ nm and its response to various ROS and RNS: $H_2O_2$, $NO_2^-$, $O_2^{|-}$, $OH^|$, TBHP, GSH, $TBO^|$ GSSG and NOC-5.

As seen in FIG. 6 and FIG. 7, quite a few ROS species caused "turn-on" fluorescence response of RTMI, including superoxide ($O_2^-$), hydrogen peroxide, peroxynitrite (generated by SIH 1), hydroxyl and butoxyl radicals. The broad response of RTMI towards these ROS species suggests that RTMI is a general ROS sensor.

Thus, specific compositions and methods of a turn-on near infrared fluorescent probes for imaging lysosomal ROS in live cells at subcellular resolution have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

REFERENCES

1. Wang, X. et al. (2013) "Imaging Ros Signaling in Cells and Animals," *J. Mol. Med.* 91(8), 917-927.
2. Winterbourn, C. C. (2008) "Reconciling the Chemistry and Biology of Reactive Oxygen Species," *Nat. Chem. Biol.* 4(5), 278-286.
3. Barnham, K. J. et al. (2004) "Neurodegenerative Diseases and Oxidative Stress," *Nat. Rev. Drug Discovery* 3(3), 205-214.
4. Kundu, K. et al. (2009) "Hydrocyanines: A Class of Fluorescent Sensors That Can Image Reactive Oxygen Species in Cell Culture, Tissue, and in Vivo," *Angew. Chem. Int. Ed.* 48(2), 299-303.
5. Lebedeva, I. V. and Patton, W. F. "Profiling Reactive Oxygen, Nitrogen and Halogen Species," United States Patent Application Publication Number US 2010-0081159 A1, application Ser. No. 12/286,103, filed Sep. 26, 2008. (published Apr. 1, 2010).
6. Kim, D. et al. (2015) "Visualization of Endogenous and Exogenous Hydrogen Peroxide Using a Lysosome-Targetable Fluorescent Probe," *Sci. Rep.* 5.

We claim:

1. A compound with the structure:

2. A method of monitoring reactive oxygen species, comprising:
   a) providing
      i) a fluid comprising at least one reactive oxygen species;
      ii) a fluorescent sensor compound comprising the formula of:

b) introducing said fluorescent sensor compound into said fluid;
   c) collecting fluorescent light data from said fluorescent sensor compound; and
   d) producing a superior spatial resolution photo image of said biological system using said fluorescent light data.

3. The method of claim 2, wherein said fluid comprises a biological fluid system comprising basal levels of a plurality of reactive oxygen species.

4. A method for profiling the status of biologically reactive oxygen species in living cells or subcellular organelles, or both, said method comprising the steps of:
   a) providing:
      i) at least one sample of said living cells comprising a plurality of cellular organelles; and
      ii) a selective reactive species indicator probe for detecting a plurality of biologically reactive species selected from the group consisting of specific reactive oxygen species and specific reactive nitrogen species, wherein said reactive indicator probe is:

b) contacting said sample with said selective indicator probe, wherein said probe generates fluorescent signals; and
   c) measuring said fluorescent signals, thereby providing a profile status of said plurality of biologically reactive species.

5. The method of claim 4, wherein said living cells are isolated from a biological material selected from a tissue, an organ or an organism.

6. The method of claim 4, wherein said subcellular organelles are selected from the group consisting of mitochondria, peroxisomes, cytosol, vesicles, lysosomes, plasma membranes, chloroplasts, nuclei, nucleoli, inner mitochondrial matrices, inner mitochondrial membranes, intermembrane spaces, outer mitochondrial membranes, secretory vesicles, endoplasmic reticuli, golgi bodies, phagosomes, endosomes, exosomes, plasma membranes, microtubules, microfilaments, intermediate filaments, filopodia, ruffles, lamellipodia, sarcomeres, focal contacts, podosomes, ribosomes, microsomes, lipid rafts, nuclear membranes, chloroplasts or cell walls, and combinations thereof.

7. The method of claim 4, wherein said probe reacts with reactive oxygen species (ROS) selected from the group consisting of superoxide ($O_2\bullet-$), hydrogen peroxide ($H_2O_2$), peroxynitrite (ONOO—), hydroxyl radical (HO$\bullet$), tert-butoxide (TBO), tert-butyl hydroperoxide (TBHP), and combinations thereof.

8. The method of claim 4, wherein said probe localizes within at least one of said subcellular organelle.

9. The method of claim 4, wherein said profile status comprises a basal level profile of a plurality of biological reactive species levels.

10. The method of claim 4, wherein said plurality of biological reactive species levels are subcellular organelle biological reactive species levels.

* * * * *